US006159727A

United States Patent [19]

Bochkariov

[11] Patent Number: 6,159,727

[45] Date of Patent: Dec. 12, 2000

[54] HYBRIDIZATION CHAMBER

[75] Inventor: Dmitry Bochkariov, Mountain View, Calif.

[73] Assignee: Clontech Laboratories, Inc., Palo Alto, Calif.

[21] Appl. No.: 09/326,746

[22] Filed: Jun. 4, 1999

[51] Int. Cl.[7] .................... C12M 1/34

[52] U.S. Cl. .................... 435/287.2; 435/91.2; 435/288.1; 435/810; 435/975

[58] Field of Search .................... 435/6, 91.2, 287.2, 435/287.9, 288.1, 810, 975

[56] References Cited

U.S. PATENT DOCUMENTS

| | | | |
|---|---|---|---|
| 5,380,492 | 1/1995 | Seymour | 422/101 |
| 5,455,180 | 10/1995 | Reid | 435/288.1 |
| 5,955,351 | 9/1999 | Gerdes et al. | 435/287.2 |

OTHER PUBLICATIONS

D. Bassett, Jr., et al., "Gene expression informatics–it's all in your mine," *Nature Genetics*, (Jan. 1999), vol. 21(1):51–55.

D. Bowtell, et al., "Options available–from start to finish–for obtaining expression data by microarray," *Nature Genetics*, (Jan. 1999), vol. 21(1):25–32.

P. Brown, et al., "Exploring the new world of the genome with DNA microarrays," *Nature Genetics*, (Jan. 1999), vol. 21(1):33–37.

A. Chakravarti, et al., "Population genetics–making sense out of sequence," *Nature Genetics*, (Jan. 1999), vol. 21(1):56–60.

V. Cheung, et al., "Making and reading microarrays," *Nature Genetics*, (Jan. 1999), vol. 21(1):15–19.

K. Cole, et al., "The genetics of cancer–a 3D model," *Nature Genetics*, (Jan. 1999), vol. 21(1):38–41.

C. Debouck, et al., "DNA microarrays in drug discovery and development," *Nature Genetics*, (Jan. 1999), vol. 21(1):48–50.

D. Duggan, et al., "Expression profiling using cDNA microarrays," *Nature Genetics*, (Jan. 1999), vol. 21(1):10–14.

J. Hacia, et al., "Resequencing and mutational analysis using oligonucleotide microarrays," *Nature Genetics*, (Jan. 1999), vol. 21(1):42–47.

R. Lipshutz et al., "High density synthetic oligonucleotide arrays," *Nature Genetics*, (Jan. 1999), vol. 21(1):20–24.

E. Southern, et al., "Molecular interactions on microarrays," *Nature Genetics*, (Jan. 1999), vol. 21(1):5–9.

*Primary Examiner*—David A. Redding
*Attorney, Agent, or Firm*—Bozicevic, Field & Francis LLP; Bret Field

[57] ABSTRACT

Hybridization chambers suitable for use in binding, e.g. hybridization, assays are provided. The subject chambers comprise an elongate container, a block element and a cap, where each of the components is preferably injection molded. Also provided are methods of using the subject chambers and kits that include the subject chambers. The subject chambers find use in a variety of applications, particularly in hybridization assays in which small sample volumes are employed.

21 Claims, 2 Drawing Sheets

HYBRIDIZATION CHAMBER

INTRODUCTION

1. Technical Field

The field of this invention is nucleic acid hybridization.

2. Background of the Invention

In vitro hybridization reactions between nucleic acids play a fundamental role in a variety of applications in the biotechnological, medical and related fields. Specific applications in which such reactions occur include research and diagnostic procedures.

In in vitro hybridization reactions, hybridization is carried out between support-bound nucleic acids and complementary nucleic acids which are free in solution. To provide for the appropriate hybridization conditions, the support having the bound nucleic acids is typically immersed in a solution that, during hybridization, includes the complementary nucleic acids.

Hybridization reactions are typically carried out in structures, e.g. wells, bottles, etc., which provide for containment of the solution and substrate during the reaction. A variety of hybridization structures have been developed in the past, where such structures include wells, glass bottles, etc.

However, there continues to be an interest in the development of new structures or vessels in which hybridization may be carried out. Of particular interest would be the development of a hybridization container that includes a minimum of components, provides for a small hybridization reaction volume, and can be produced economically.

SUMMARY OF THE INVENTION

Hybridization chambers suitable for use in binding, e.g. hybridization, assays are provided. The subject chambers comprise an elongate container, a block element and a cap, where each of the components is preferably injection molded. Also provided are methods of using the subject chambers and kits that include the subject chambers. The subject chambers find use in a variety of applications, particularly in hybridization assays in which small sample volumes are employed.

DESCRIPTION OF THE SPECIFIC EMBODIMENTS

Figure 1:
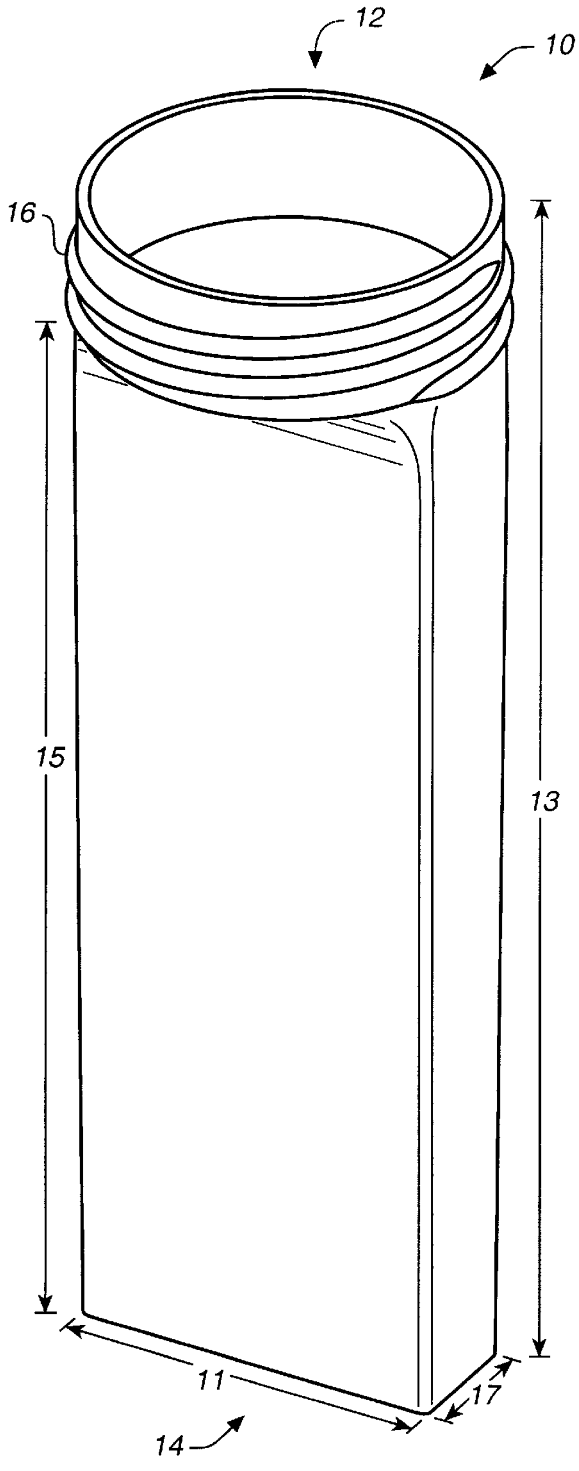
FIG. 1 provides a three-dimensional view of the elongate container element of a hybridization chamber according to the subject invention.

Hybridization chambers suitable for use in binding, e.g. hybridization, assays are provided. The subject chambers comprise an elongate container, a block element and a cap, where each of the components is preferably injection molded. Also provided are methods of using the subject chambers and kits that include the subject chambers. The subject chambers find use in a variety of applications, particularly in hybridization assays in which small sample volumes are employed.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

HYBRIDIZATION CHAMBERS

As mentioned above, the hybridization chambers of the subject invention include the following components: an elongate container; a block component; and a sealing means. Each of these components is now described in greater detail.

Elongate Container

The elongate container of the hybridization chamber has an open proximal end and a closed distal end so as to produce a substantially enclosed first space, with the only opening being at the open first end. As this container component is elongate, the length of the container is substantially longer than the width. As such, the length is at least about 1.5 times longer, usually at least about 2 times longer and more usually at least about 3 times longer, but will usually not exceed about 5 times longer than the width (as measured at the widest portion of the container). The longest width of the container ranges from about 20 to 50 mm and usually from about 25 to 35 mm. As such, the length of the container from the proximal to the distal end typically ranges from about 50 to 150 mm, usually from about 70 to 120 mm and more usually from about 90 to 100 mm. The volume of the first space bounded by the walls of the container ranges from about 10 to 100 ml, usually from about 20 to 50 ml and more usually from about 25 to 30 ml.

The elongate container may be further characterized in that the cross-sectional area at the open proximal end of the container is greater than the cross-sectional area at the distal, closed end of the container. The open proximal end of the container can have a variety of different shapes, including rectangular, elipsoid, circular, etc. In many preferred embodiments, the cross-sectional shape at the open proximal end of the container is circular while the cross-sectional shape at the distal end of the container is square or rectangular, usually rectangular.

The distal, closed end of the container can have a variety of different configurations, so long as the distal end forms a closed "bottom" to the container. Thus, the distal end can have a rounded configuration (analogous to a test tube), and angular configuration, a flat configuration (as shown in the accompanying figures), and the like.

In those embodiments having a square or rectangular cross-sectional shaped distal end, four walls will extend for a substantial portion of the length from the distal end, where by substantial length is meant at least about 50%, usually at least about 70% and more usually at least about 80% of the length of the container. The thickness of the walls from the inner surface of the container to the outer surface of the container typically ranges from about 0.5 to 2.0 mm, usually from about 0.8 to 1.5 mm.

In many embodiments, on the inner surface of at least one of the walls of the container are spacers, e.g. ridges or rails, that provide supports for the block element and define the second space of the chamber, as described in greater detail infra. In a preferred embodiment, at least one inner surface of a wall of the container has two parallel rails, positioned at the edge of the wall adjacent to the bounding walls, running along the substantial length of the wall, where the height of the rails ranges from about 0.4 to 2.5 mm, usually from about 0.6 to 1.5 mm and the width of the rails ranges from about 0.5 to 5.0 mm, usually from about 1.0 to 3.0 mm.

In many preferred embodiments where the open proximal end of the container is circular, screw threads are positioned to interface with a cap, described in greater detail infra, where the cap screws onto the open end to seal the container.

Generally, the elongate container is fabricated from a polymeric material such that it can be produced by injection molding. The container may be fabricated from a variety of different polymeric materials, where suitable polymeric materials are ones that are relatively inert with respect to the binding assay to be performed in the hybridization chamber, i.e. they do not interact in detrimental ways with reagents and/or solutions employed in the binding assays. Polymeric materials from which the subject containers may be fabricated include those that are capable of being injection molded, where representative polymeric materials are: polypropylene, polystyrene, polycarbonate, polysulphone, TEFLON™, other fluorocarbons, and the like.

Block Element

A critical component of the subject hybridization chambers is the block element which is positioned inside the elongate container in a manner sufficient to (in combination with a solid support such as a glass microscope slide) form a second, hybridization space out of the first space defined by the walls of the container described above. The volume of the second space is substantially smaller than the volume of the first space, typically being at least about 3 fold smaller, usually at least about 5 fold smaller and more usually at least about 10 fold smaller. As such, the volume of the second space produced in the container by the presence of the block element in the container ranges from about 0.2 to 10 ml, usually from about 0.5 to 5.0 ml and more usually from about 0.5 to 2.0 ml. The block element is further characterized in that it has a sufficient volume to substantially fill the entire amount of the first space of the container not occupied by the second space. As such, the volume of the block element typically ranges from about 10 to 90 ml, usually from about 20 to 30 ml. The length of the block element ranges from about 50 to 150 mm, usually from about 90 to 100 mm and the width of the block element ranges from about 20 to 50 mm, usually from about 25 to 35 mm.

The block element is further characterized by being configured to fit snugly within the elongate container, e.g. its shape corresponds to the inner surfaces of the container to leave substantially no void spaces apart from the second space. As such, in the preferred embodiments of the invention the block element has a rectangular distal end and circular proximal end, where four walls extend from the rectangular distal end for a substantial portion of the length of the block element.

A critical feature in one embodiment of the block element is the presence of a planar surface which is configured to support a substrate to which members of the binding assay are stably associated. While the planar support may have a variety of configurations depending on the nature of the substrate, in those preferred embodiments in which the chamber is designed for use with substrates having conventional slide shapes, the planar surface is rectangular, with a length ranging from about 50 to 120 mm, usually from about 70 to 80 mm, and a width ranging from about 15 to 30 mm, usually from about 20 to 30 mm.

In another embodiment of the block element, the surface of the block element that is designed for supporting the substrate includes rails or ridges on at least a portion of its outer periphery, e.g. along the periphery of the two longitudinal sides, which serve to support the substrate above the rest of the surface and form a hybridization space when the support is positioned on top of the ridges. The ridges are analogous to those described in greater detail below. In this embodiment, the remainder of the surface need not necessarily be planar.

At the proximal end of the block element is a groove which, when the block is positioned in the elongate container, forms a fluid passageway from the proximal open end of the container into the second space or hybridization space. In a preferred embodiment, the groove is configured to receive a pipette tip. As such, the width of the groove generally ranges from about 2 to 10 mm, usually from about 4 to 6 mm.

The block element may include additional features, such as additional indentations at the proximal end that are useful for grabbing onto the block element to remove it from the elongate container. Such features find use in that the block element typically fits sufficiently snugly into the elongate container such that it will not fall out of the container upon inversion of the container. Instead, some additional force beyond the force of gravity must be applied to the block element to insert and remove it from the container.

In the broadest sense, the block element may be a solid material or a hollow material. However, the block element is typically a solid polymeric material produced by injection molding. The polymeric material from which the block element is injection molded may be one of a variety of materials, where suitable materials include: polypropylene, polystyrene, polycarbonate, polysulphone, TEFLON™ and the like. The material may further include one or more foaming agents that prevent the creation of sinks or other irregularities during the injection molding process.

Removable Sealing Means

In addition to the block and container components, the hybridization container further comprises a removeable sealing means for sealing or isolating the contents of the container from the external environment of the container. In the broadest sense, sealing means may be any of a number of structures, such as a lid, film, cap, etc., where the sealing means may snap on, glue on, screw on etc., with the only limitation being that, when in place, the sealing means should substantially prevent fluid leakage from the inside of the container. In a preferred embodiment, the sealing means is a threaded cap that is capable of being screwed onto the open, proximal end of the container, where the open proximal end is characterized by the presence of corresponding threads on its outer surface.

Substrates

In certain embodiments, the chamber further comprises a substrate present on the planar surface of the block element in the container, where the substrate may or may not have an array of binding agents, e.g. nucleic acids, peptides, proteins, antibodies, etc., present on its surface, or tissue sections present on its surface, cells adhered to the surface, and the like. The substrates may take a variety of configurations ranging from simple to complex, depending on the intended use of the array. Thus, the substrate could have an overall slide or plate configuration, such as a rectangular or disc configuration. In preferred embodiments, the substrate will have a rectangular cross-sectional shape, having a length of from about 10 mm to 200 mm, usually from about 40 to 150 mm and more usually from about 75 to 125 mm and a width of from about 10 mm to 200 mm, usually from about 20 mm to 120 mm and more usually from about 25 to 80 mm, and a thickness of from about 0.01 mm to 5.0 mm, usually from about 0.1 mm to 2 mm and more usually from about 0.2 to 1.2 mm. Thus, in one embodiment the support may have a micro-titre plate format, having dimensions of approximately 125×85 mm. There can be one or more substrates in the container, where in many embodiments the number of substrates present in the container is one or two.

The substrates of the subject arrays may be fabricated from a variety of materials. The materials from which the substrate is fabricated should ideally exhibit a low level of non-specific binding during hybridization events. In many situations, it will also be preferable to employ a material that is transparent to visible and/or UV light. The substrate may be flexible or rigid. For flexible substrates, materials of interest include: nylon, both modified and unmodified, nitrocellulose, polypropylene, and the like, where a nylon membrane, as well as derivatives thereof, is of particular interest in this embodiment. For rigid substrates, specific materials of interest include: glass; plastics, e.g. polytetrafluoroethylene, polypropylene, polystyrene, polycarbonate, polysulfone and blends thereof, and the like; metals, e.g. gold, platinum, aluminum, and the like; etc.

Of particular interest in many embodiments are hybridization chambers in which the elements are designed to be used in conjunction with nucleic acid arrays as described in: U.S. patent application Ser. No. 08/859,998; U.S. patent application Ser. No. 08/974,298; U.S. patent application Ser. No. 08/859,998; U.S. patent application Ser. No. 08/974,298; U.S. patent application Ser. No. 09/225,998; U.S. application Ser. No. 09/221,480; U.S. application Ser. No. 09/222,432; U.S. application Ser. No. 09/222,436; U.S. application Ser. No. 09/222,437; U.S. application Ser. No. 09/222,251; U.S. application Ser. No. 09/221,481; U.S. application Ser. No. 09/222,256; U.S. application Ser. No. 09/222,248; U.S. application Ser. No. 09/222,253; U.S. application Ser. No. 60/104,179; the disclosures of which are incorporated herein by reference.

A Preferred Embodiment

The hybridization chambers having now been described in general terms, further details of the subject invention in terms of a specific embodiment will now be provided in terms of the figures. Turning now to FIG. 1, a three-dimensional representation of elongate container 10 is provided. Elongate container 10 has an open proximal end 12 and a closed distal end 14. Open proximal end 12 has a circular cross-sectional shape and an diameter ranging from about 20 to 50 mm, usually from about 25 to 35 mm. Closed distal end 14 has a rectangular cross sectional shape having an area ranging from about 1 to 20 cm , usually from about 2 to 5 $cm^2$. The longest cross-sectional dimension 11 of the distal end 14 is substantially the same length as the inner diameter of the proximal end 12. The length of the elongate container 13 ranges from about 70 to 120 mm, usually from about 90 to 100 mm. A substantial portion 15 of the elongate container has a rectangular cross-sectional shape, where the length of this portion 15 ranges from about 50 to 100 mm, usually from about 70 to 80 mm. The shorter cross-sectional dimension 17 of the distal end has a length ranging from about 4 to 20 mm, usually from about 5 to 12 mm. On the outer surface of the proximal end of the container are screw threads 16, which interact with a cap, not shown, to at least substantially seal the inner contents of the container from the outside environment of the container, such that liquid and gases do not pass between the inner space of the container and the outer environment.

Figure 2:
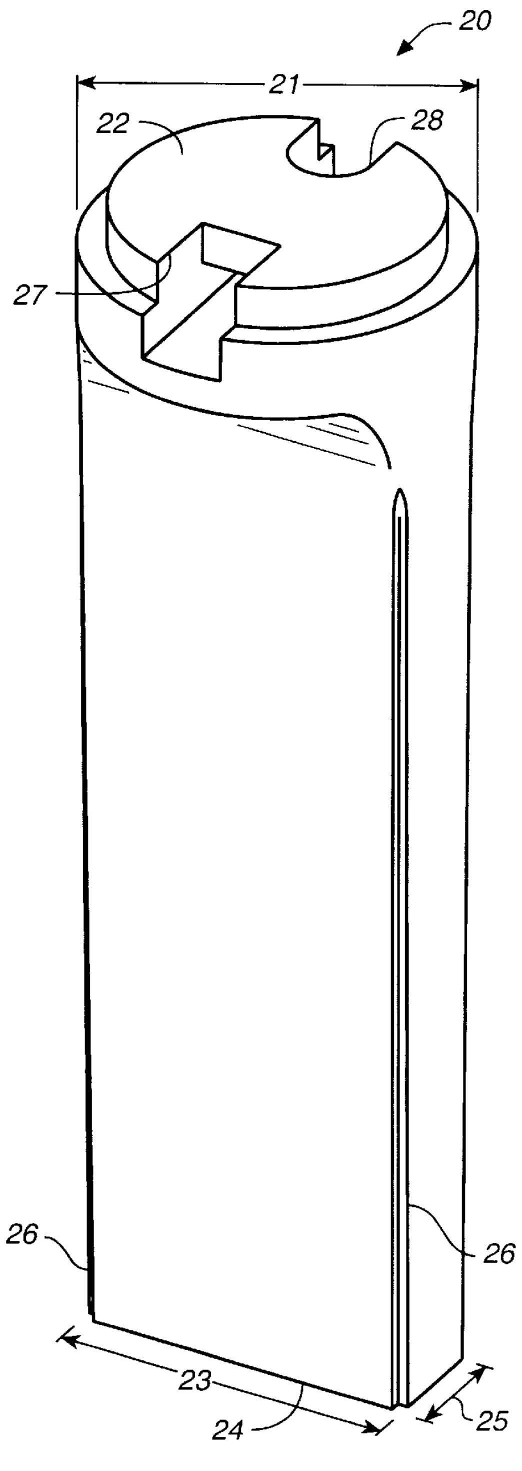
FIG. 2 provides a three-dimensional view of the block element of a hybridization chamber according to the subject invention.

FIG. 2 provides a three-dimensional view of a block element designed for use with the elongate container shown in FIG. 1. Block element 20 is a solid polymeric material and has a proximal end 22 and a distal end 24. Proximal end 22 has a circular cross-sectional shape, where the diameter 21 ranges from about 20 to 50 mm, usually from about 20 to 35 mm. The longest cross-sectional dimension 23 of the block element at the distal end 24 ranges from about 15 to 50 mm, usually from about 20 to 35 mm, while the shortest cross-sectional dimension 25 at the distal end ranges from about 2 to 18 mm, usually from about 3 to 10 mm. The block element includes indentations 26 running for a substantial length of the block element which conform to the rails or ridges present on the inner walls of the elongate container and thereby serve to make the block element better conform to the inner spatial configuration of the elongate container. On the side of the block element not shown is a substantially planar rectangular surface having an area ranging from about 8 to 50 $cm^2$, usually from about 15 to 20 $cm^2$. At the proximal end 22 of the block element is a groove 28 that allows for flow into the hybridization space produced in the elongate container above the substrate upon placement of the block element into the elongate container. Notch 27 is also present on proximal end 22, where the notch provides a place for grabbing onto the block element to pull the block element out the of elongate container.

Figure 3:
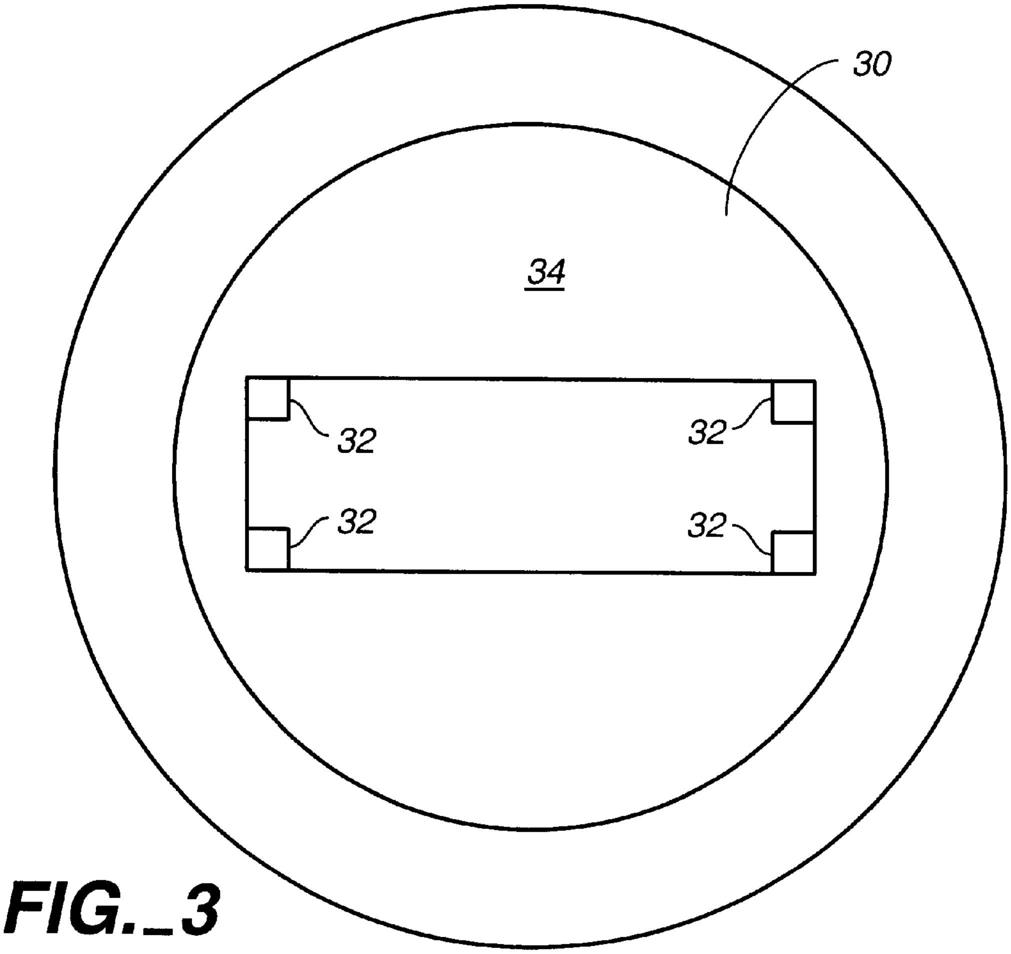
FIG. 3 provides a top view of the elongate container element of a hybridization chamber according to the subject invention.

FIG. 3 provides a top view of the elongate container. In FIG. 3 open proximal open end 30 has a circular cross-sectional shape. The inner surface extending away from the distal end 34 rapidly changes to a rectangular cross-sectional configuration, which configuration then extends for the remainder of the container to the distal end. In each comer of the portion of the container having the rectangular cross sectional configuration is a spacer or rail 32 that extends for the entire length of portion of the container having a rectangular cross-sectional dimension to the distal end. The spacers or rails have a height (the length of the side perpendicular to the longest cross-sectional dimension) that ranges from about 0.4 to 2.0 mm, usually from about 0.6 to 1.4 mm and a width (the length of the side perpendicular to the shortest cross-sectional dimension) that ranges from about 0.5 to 3.0 mm, usually from about 0.8 to 2.0 mm.

UTILITY

The subject hybridization chambers find use in binding assays in which members of specific binding pairs interact, where the interaction is of import to the assay. Any of a number of binding assays may be performed in the subject hybridization chambers, where typically a first member of a binding pair is stably associated with the surface of a planar substrate present on the planar surface of the block element and a second member of the binding pair is free in solution present in the second or hybridization space of the container. A variety of binding assays may be performed in the subject hybridization chambers, where the binding pair members may be: ligands and receptors; antibodies and antigens; complementary nucleic acids; and the like. Of particular interest in many embodiments are hybridization assays in which the binding pair members are complementary nucleic acids. Accordingly, methods of using the hybridization chamber of the subject invention will be further described in terms of hybridization assays. However, the principles reviewed below apply to other types of binding assays, like immunoassay, immunocytochemistry, in situ hybridization, etc., as will be appreciated by one of the skill in the art.

For hybridization assays, the first step is to position the substrate having nucleic acids stably associated on one of its surfaces onto the planar surface of the block element. The nucleic acids may be stably associated with the substrate surface a number of different ways, including covalent and non-covalent binding, where the only requirement is that nucleic acids be sufficiently bound to the surface of the support so as not to dislodge during the hybridization assay steps. Of particular interest are nucleic acid arrays. The nucleic acid arrays employed in the subject hybridization assays have a plurality of nucleic acid spots, and preferably polynucleotide spots, stably associated with a surface of a solid support. Nucleic acid arrays finding use in the subject invention therefore include nucleic acid biochips, e.g. cDNA biochips, cRNA biochips, polynucleotide biochips, oligonucleotide biochips, and the like. Of particular interest in many embodiments are the nucleic acid arrays described in: U.S. patent application Ser. No. 08/859,998; U.S. patent application Ser. No. 08/974,298; U.S. patent application Ser. No. 08/859,998; U.S. patent application Ser. No. 08/974,298; U.S. patent application Ser. No. 09/225,998; U.S. application Ser. No. 09/221,480; U.S. application Ser. No. 09/222,432; U.S. application Ser. No. 09/222,436; U.S. application Ser. No. 09/222,437; U.S. application Ser. No. 09/222,251; U.S. application Ser. No. 09/221,481; U.S. application Ser. No. 09/222,256; U.S. application Ser. No. 09/222,248; U.S. application Ser. No. 09/222,253; U.S. application Ser. No. 60/104,179; the disclosures of which are incorporated herein by reference.

After the substrate is positioned onto the planar surface of the block element, the block element is introduced into the container, whereby a working space is formed between the surface of the substrate and the inner surface of one wall of the container and the remaining volume of the container is occupied by the block element in such a manner as leave substantially no other void spaces. The working space discussed above is the second or hybridization space, and serves as the location in which the hybridization events will occur.

Following introduction of block element and substrate into the container, a hybridization solution comprising the complementary nucleic acids (or at least potentially complementary nucleic acids or other substances depending on the nature of the assay being performed) is then introduced into the second or hybridization space of the container. The solution is introduced through the groove located at the proximal end of the block element, conveniently by pipette.

Following introduction of the solution or fluid, the sealing means, e.g. cap, is then positioned over the open proximal end of the container, e.g. screwed onto the proximal end, thereby isolating the contents of the container from the external environment. Hybridization is then allowed to proceed.

Following hybridization, the cap is removed. Next, one or more washing steps are generally performed to remove unbound nucleic acid, or other substances, depending on the assay being performed, which steps are followed by detection of hybridized nucleic acids or other interaction(s). These additional steps may be performed in the container or the substrate can be removed and the steps carried out in a different container.

Principles of hybridization assays are well known to those of skill in the art and are reviewed in Sambrook et al., Molecular Cloning: A Laboratory Manual (Cold Spring Harbor Press)(1989).

Although the above described assays have been described primarily in terms of hybridization assays, one of skill in the art will readily see that analogous binding assays or methods can be performed through execution of substantially the same steps. Thus, for ligand/receptor binding assays, a substrate having ligand stably associated therewith and the block element are introduced into the container, followed by introduction of a solution comprising the receptor into the second space formed by the block element and the container. After a sufficient period of incubation and any desired washing, the substrate is removed from the container and the presence of ligand receptor complexes is detected.

KITS

Also provided are kits comprising the subject hybridization chambers. At the minimum, the kits include at least one hybridization chamber according to the subject invention. The kits may further comprise one or more additional components, reagents, solutions etc., required for a specific type of binding assay which is to be performed in the chamber. For example, in kits designed for hybridization assays, the kits may comprise dNTPs and/or rNTPs, which may be either premixed or separate, one or more uniquely labeled dNTPs and/or rNTPs, such as biotinylated or fluorescently tagged dNTPs, enzymes, such as reverse transcriptases, DNA polymerases, and the like, various buffer mediums, e.g. hybridization and washing buffers, prefabricated probe arrays, labeled probe purification reagents and components, like spin columns, etc., signal generation and detection reagents, e.g streptavidin-alkaline phosphatase conjugate, chemifluorescent or chemiluminescent substrate, and the like.

The following examples are offered by way of illustration and not by way of limitation.

EXPERIMENTAL

A hybridization experiment is performed using a standard 25×75×1 mm microscope glass slide as a solid planar support. On the microscope slide a cDNA array as prefabricated by depositing approximately 250 different individual cDNAs corresponding to certain human genes. The probe for the hybridization experiment was prepared starting from MRNA sample prepared and purifeed from a human placenta tissue sample. The labeled probe was prepared utilizing a reverse transcription reaction in the presence of a mixture of all necessary deoxynucleotidetriphosphates also containing fluorescently labeled nucleotide. In this particular experiment the labeled nucleotide was Cy3-dUTP, but a variety of other labeled nucleotides can be employed, including ones labeled with radioactive isotopes such as [$^{32}$p]. Fluorescently labeled cDNA probe was denatured at 95° C. for 2 minutes and then mixed with 1 ml of hybridization solution (5×SSC, 0.1% SDS) pre-heated at 50° C. This mixture was introduced into the hybridization chamber preliminarily assembled with the microscope slide containing the cDNA array in such a way that the array is facing the working or hybridization space inside the chamber. The chamber was sealed with a screw cap and incubated at 50° C. for 16 hours. After the incubation, the screw cap was removed, the insert pulled out and the array washed 2 times with 2×SSC, 0.1%SDS, on time with 1×SSC, rinsed with water, dried and scanned in a fluorescent scanner (ScanArray 3000(General Scanning, Inc.)).

The above example illustrates that the chamber can also be used for any other assay that employs a microscope slide as a solid support, like in situ hybridization assays, histology or cytology assays, etc.

It is evident from the above results and discussion that the subject hybridization chambers provide a number of advantages. First, all of the elements of the subject hybridization chambers can be injection molded from polymeric materials, making them inexpensive to produce. Second, the design of the subject chambers provides for an extremely small hybridization volume, which is particularly useful when small sample volumes are employed, e.g. where the sample is rare and/or expensive to produce. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A hybridization chamber comprising:

(a) an elongate container having an open proximal end and a closed distal end and enclosing a first space;

(b) a block element having at least one planar surface, wherein said block element is positioned inside said container in a manner sufficient to produce a second space in said first space, wherein said second space has a volume that is substantially less than said first space;

(c) a means for introducing fluid into said second space; and (d) a means for sealing said open proximal end.

2. The hybridization chamber according to claim 1, wherein at least said elongate container and said block element are fabricated from a polymeric material.

3. The hybridization chamber according to claim 2, wherein said elongate container and said block element are injection molded.

4. The hybridization chamber according to claim 1, wherein said means for introducing fluid into said second space is a groove on said block element.

5. The hybridization chamber according to claim 1, wherein said hybridization chamber further includes at least one planar substrate positioned on said planar surface of said block element.

6. A hybridization chamber comprising:

(a) an injection molded polymeric elongate container having an open proximal end and a closed distal end and enclosing a first space, wherein the cross-sectional area of said open end is greater than the cross-sectional area of said distal end;

(b) an injection molded block element having at least one planar surface, wherein said block element is positioned inside said container in a manner sufficient to produce a second space in said first space, wherein said second space has a volume that is substantially less than said first space;

(c) a groove on said injection molded block element, wherein said groove provides for fluid flow from said open proximal end to said second space; and (d) a cap for sealing said open proximal end.

7. The hybridization chamber according to claim 6, wherein said open proximal end of said elongate container has a circular cross-sectional shape.

8. The hybridization chamber according to claim 6, wherein said closed distal end of said elongate container has a rectangular cross-sectional shape.

9. The hybridization chamber according to claim 6, wherein said injection molded block element occupies substantially all of said first space not occupied by said second space.

10. The hybridization chamber according to claim 6, wherein said elongate container further comprises spacers on at least one inner wall.

11. The hybridization chamber according to claim 10, wherein said spacers are rails extending along a substantial length of said elongate container.

12. A hybridization chamber comprising:

(a) an injection molded polymeric elongate container enclosing a first space and having:
   (i) a circular, open proximal end;
   (ii) a rectangular, closed distal end;
   (iii) parallel rails on at least one inner surface of said elongate container extending from said distal end to point prior to said proximal end;

(b) an injection molded polymeric block element positioned inside said container in a manner sufficient to produce a second space in said first space, wherein said second space has a volume that is substantially less than said first space, wherein said block element is further characterized by having:
   (i) at least one planar surface;
   (ii) a circular proximal end;
   (iii) a rectangular distal end; and
   (iv) a groove in said circular end that provides for passage of fluid from said open, proximal end of said elongate container into said second space; and (c) a cap for sealing said open proximal end.

13. The hybridization chamber according to claim 12, wherein the volume of said first space ranges from about 15 to 25 ml.

14. The hybridization chamber according to claim 12, wherein the volume of said second space ranges from about 4 to 5 ml.

15. The hybridization chamber according to claim 12, wherein said block element has a volume ranging from about 15 to 20 ml.

16. The hybridization chamber according to claim 12, wherein said second space comprises a substrate which leaves a hybridization volume of from about 0.5 to 2.0 ml.

17. The hybridization chamber according to claim 12, wherein said hybridization chamber further comprises a planar substrate positioned on said planar surface of said block element.

18. A method of performing a binding assay, the improvement comprising:

carrying out said binding assay in the hybridization chamber according to claim 1.

19. The method according to claim 18, wherein said binding assay is a hybridization assay.

20. A kit for use in performing a binding assay, said kit comprising:

a hybridization chamber according to claim 1.

21. The kit according to claim 20, wherein said kit further comprises a hybridization solution.

* * * * *